United States Patent [19]

Koizumi et al.

[11] 4,423,331
[45] Dec. 27, 1983

[54] METHOD AND APPARATUS FOR INSPECTING SPECIMEN SURFACE

[75] Inventors: Mitsuyoshi Koizumi; Nobuyuki Akiyama; Yoshimasa Oshima, all of Yokohama, Japan

[73] Assignee: Hitachi, Ltd., Tokyo, Japan

[21] Appl. No.: 242,483

[22] Filed: Mar. 11, 1981

[30] Foreign Application Priority Data

Mar. 12, 1980 [JP] Japan .................................. 55-30396

[51] Int. Cl.$^3$ ........................................... G01N 21/88
[52] U.S. Cl. .................................... 250/572; 356/446
[58] Field of Search ............... 250/570, 571, 572, 562, 250/563; 356/445, 446, 430, 431

[56] References Cited

U.S. PATENT DOCUMENTS

| | | | |
|---|---|---|---|
| 3,659,950 | 5/1972 | Troll et al. | 356/430 |
| 3,879,131 | 4/1975 | Cuthbert et al. | 250/572 |
| 4,095,905 | 6/1978 | Kuni et al. | 356/446 |
| 4,197,011 | 4/1980 | Hudson | 250/572 |
| 4,202,627 | 5/1980 | Suzuki et al. | 356/446 |

OTHER PUBLICATIONS

"A Laser Scan Technique for Electronic Materials Surface Evaluation" by Oswald et al., Jour. of Electronic Material, vol. 3, No. 1, 1974.

*Primary Examiner*—David C. Nelms
*Attorney, Agent, or Firm*—Antonelli, Terry & Wands

[57] ABSTRACT

A method and apparatus of inspecting a surface of a specimen for the presence of defects, foreign substance and the like are disclosed. The surface has a mark such as a cutting mark formed thereon and composed of fine grooves or recesses extending in a predetermined direction. The surface is scanned two-dimensionally with an irradiating laser beam impinging or illuminating on the specimen surface perpendicularly thereto. Those of the irregularly scattered laser light rays reflected from the specimen surface which are in a first direction perpendicular to the lengthwise direction of the mark are intercepted by a shielding member or caused to pass through regions other than a reflecting region of a reflecting mirror, while those scattered light rays which are in other directions than the first direction are directed to a photoelectric converter tube along a bypass path across the shielding member or through reflection of the mirror. A picture signal derived from the output of the photoelectric converter tube is digitalized into binary picture element signals by a sampling and binary encoding circuit, the resulting signals being then stored in a two-dimensional memory. The presence and forms of defects, foreign substances and the like on the specimen surface are discriminatively determined in dependence on particular combinations of the binary picture element signals stored in the memory.

6 Claims, 30 Drawing Figures

METHOD AND APPARATUS FOR INSPECTING SPECIMEN SURFACE

BACKGROUND OF THE INVENTION

The present invention generally relates to a method of inspecting or examining a surface of a specimen as to the presence or absence of imperfections such as defects, damages, injuries, scratches or the like and/or foreign substances such as contaminants or the like. In particular, the method according to the invention is intended to be applied to such inspection or examination of a blank or substrate material for a magnetic disc on which undesired fine topographical marks such as cutting marks are formed with a certain directivity (i.e. in a predetermined direction). The present invention also concerns an apparatus for carrying out the above-mentioned method.

Figure 1:
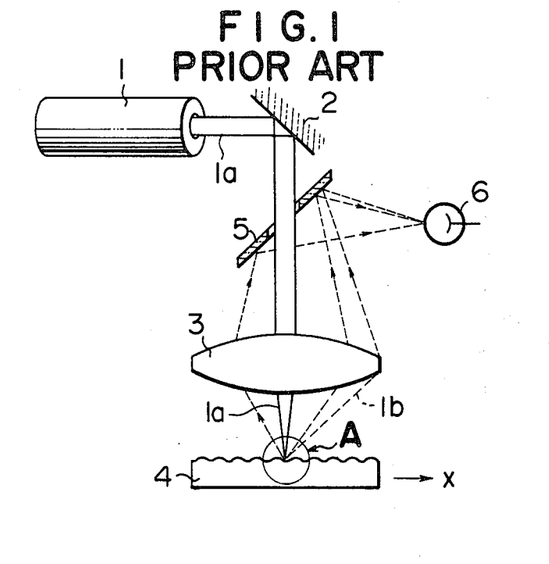
FIG. 1 shows schematically a general arrangement of a hitherto known inspecting apparatus of scattered light collecting type for detecting presence of defects, foreign materials or the like on a surface of a specimen.
Figure 2:
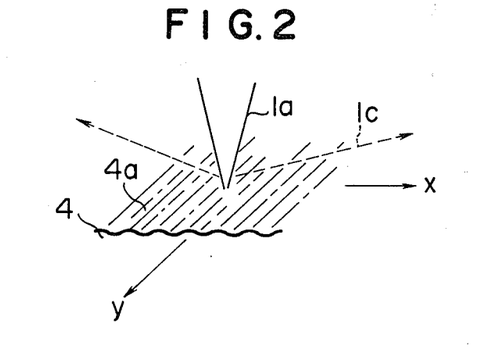
FIG. 2 illustrates irregularly scattered light reflected from a cutting mark formed in the specimen surface.
Figure 3:
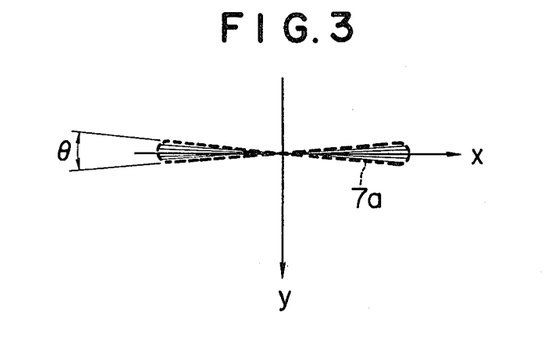
FIG. 3 shows in a polar coordinate an intensity distribution of the irregularly reflected light scattered by the mark shown in FIG. 2.
Figure 4:
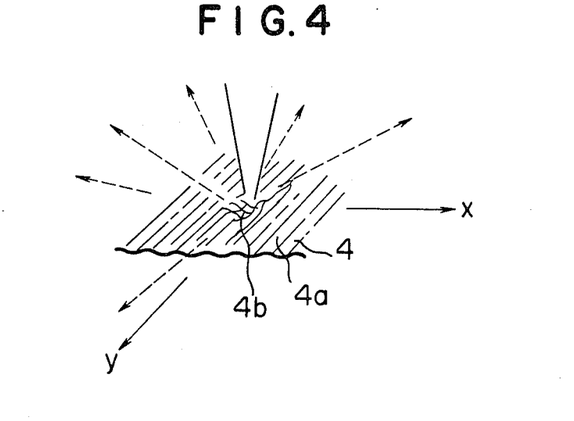
FIG. 4 is a view similar to FIG. 2 but shows irregularly reflected light scattered from an isolated or point-like defect.
Figure 5:
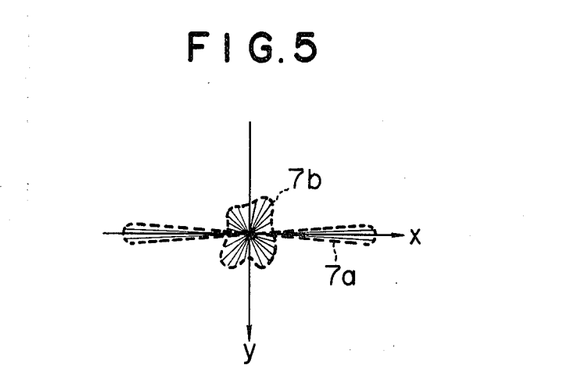
FIG. 5 shows in a polar coordinate an intensity distribution of the irregularly reflected light from the point-like defect shown in FIG. 4.
Figure 6:
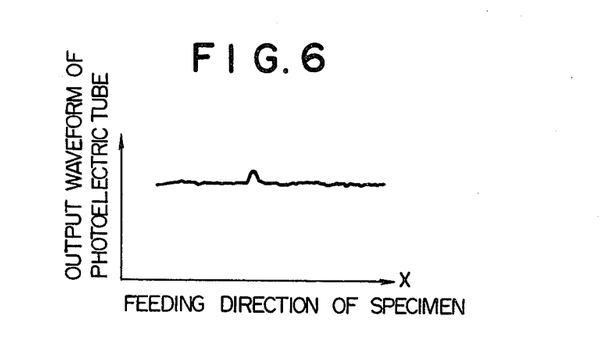
FIG. 6 graphically illustrates an output voltage signal from a photoelectric tube of the apparatus shown in FIG. 1 in response to the light scattered by a point-like surface defect.
Figure 7:
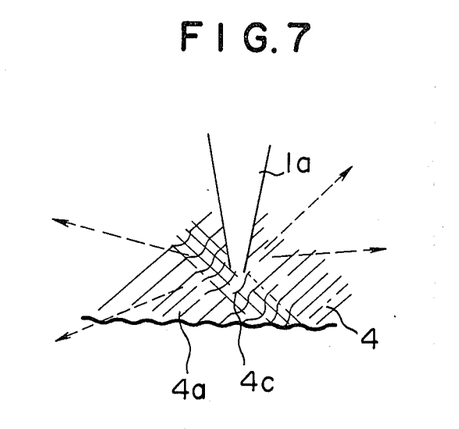
FIG. 7 shows irregularly reflected light rays scattered by a linear defect on the surface of a specimen.
Figure 8:
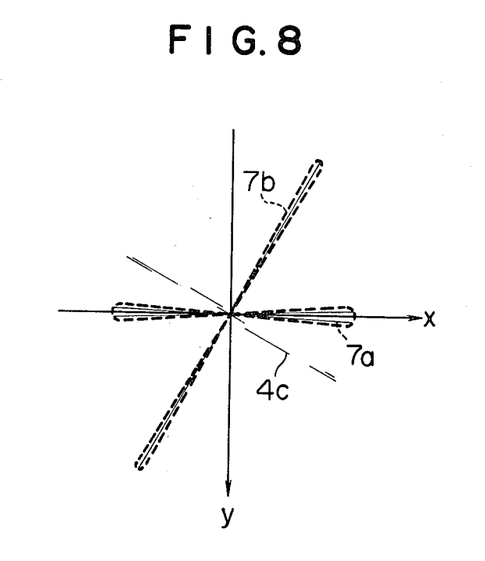
FIG. 8 shows in a polar coordinate an intensity distribution of the irregularly reflected light scattered by the linear defect shown in FIG. 7.

For having a better understanding of the invention, hitherto known methods and apparatus for detecting the imperfections or defects on specimens such as blank materials for magnetic discs will be described in some detail. FIG. 1 of the accompanying drawings shows a typical one of the conventional inspecting apparatus of a scattered light collect-type. Referring to the figure, a laser light beam $1a$ is generated by a laser oscillator 1 and directed to a surface of a specimen 4 for irradiation thereof through a mirror 2 and a lens 3. When the surface of the specimen 4 to be examined is perfectly flat or smooth, all of the laser light $1a$ undergoes normal reflection at the specimen surface and follows its incident path in reverse to the oscillator through a center hole formed in a mirror 5. When the surface of the specimen 4 is roughened, incident laser light is scattered as indicated by broken lines $1b$ with arrows and collected by the lens 3 to be directed to a photoelectric tube 6 after having been deflected by the mirror 5 having the center through-hole. When a surface of a metallic specimen 4 having cutting marks is in concern, the laser light undergoes such irregular reflection that the light is scattered in the direction (x-direction) which extends orthogonal to the cutting marks $4a$ provided on the surface in the form of fine grooves or recesses extending in the y-direction, as indicated by arrow-headed broken lines $1c$ in FIG. 2. FIG. 3 shows in a polar coordinate a distribution of intensity of light having undergone such irregular reflection. When the cutting marks are formed through grinding or the like machining, components of the irregularly scattered light rays in the x-direction lie predominantly within an angular range $\theta$ of about 1°. In other words, the irregularly reflected or scattered light exhibits a significant directivity. It is now assumed that an isolated or discrete point-like defect $4b$ such as a depression or a dimple is present on the surface of the specimen 4, as is illustrated in FIG. 4. When the diameter of the irradiating laser beam is larger than that of the isolated point-like defect $4b$, there is obtained an intensity distribution $7b$ of the irregularly reflected or scattered light, which distribution exhibits a lesser directivity, as shown in a polar coordinate in FIG. 5. The light flux $1c$ impinging on the photoelectric tube 6 thus includes the irregularly scattered light reflected from the cutting mark and the scattered light rays reflected from the isolated point-like defect $4b$, resulting in that an output voltage signal derived from the photoelectric tube 6 has a signal waveform such as illustrated in FIG. 6. In the case where a linear defect $4c$ such as scratch is present on the surface of the specimen 4 as illustrated in FIG. 7, then there is produced an intensity distribution $7b$ of the light irregularly reflected from the linear defect $4c$, which distribution exhibits a strong directivity in the direction perpendicular to the longitudinal direction of the scratch $4c$, as is illustrated in a polar coordinate in FIG. 8. In this case, the voltage signal output from the photoelectric tube 6 has a waveform similar to the one illustrated in FIG. 6.

It will be appreciated that the voltage output from the photoelectric tube 6 obtained with the defect detection system described above undergoes inevitably an offset which corresponds to the intensity of the irregularly reflected light scattered by the cutting marks, involving extremely lowered detection sensitivity for the defects such as the isolated point-like defect $4b$ and the linear defect or scratch $4c$, to a disadvantage. This is ascribable to such sensitivity characteristic of the photoelectric tube 6 that the output voltage thereof is saturated when the incident light is bright, while exhibiting a linearity in the sensitivity when the incident light is in a lower intensity range. By way of example, when a ground surface (0.05 μm R.M.S.) of an aluminium plate is inspected by irradiating with a laser beam of 50 μm in diameter through a lens of 0.4 in numerical aperture, the possibility of detecting the defect is limited to the point where the diameter and width of the defect is about 10 μm and 1 μm, respectively.

SUMMARY OF THE INVENTION

An object of the present invention is to provide a method of inspecting a surface of a specimen having a fine pattern of recesses or grooves extending in a predetermined direction which method allows presence of defects and/or foreign substance and the like to be detected with a high sensitivity and accuracy.

Another object of the invention is to provide an apparatus for carrying out the method described above.

In view of the above and other objects which will become apparent as description proceeds, it is proposed according to a feature of the invention that a major portion of the irregularly reflected laser light scattered from a mark formed in a surface of a specimen to be examined and composed of an undesired fine pattern of recesses or grooves extending in a predetermined direction (i.e. the scattered light components irregularly reflected in a direction orthogonal to the longitudinal or lengthwise direction of the mark) is intercepted by a shielding plate or caused to pass or transmit through a light transmitting portion of a reflecting mirror, while the irregularly reflected light scattered in the other directions is caused to pass through a region outside the shielding region of the shielding plate and applied to a photoelectric converter element by way of the above-mentioned reflecting mirror. With the aid of the signal output from the photoelectric converter means, presence of defects and/or foreign substances and the like of extremely small size on the specimen surface having the mark can be detected with an increased sensitivity and reliability.

According to another aspect of the invention, there is provided an apparatus for inspecting or examining a surface of a specimen as to the presence of detects such as point defect, scratch or the like and/or foreign substances, which surface has a mark or the like including fine recesses formed in a predetermined direction. The apparatus comprises laser beam projecting means for irradiating the specimen surface with a laser light beam along an optical axis perpendicular to the specimen surface, scanning means for scanning the specimen surface with the laser beam in a two-dimensional pattern by moving one of the laser beam and the specimen relative to the other, photoelectric converter elements, a first mirror disposed so that the center of the mirror is positioned on the perpendicular optical axis and having an inner ellipsoidal mirror surface of revolution or an inner paraboloidal mirror surface of revolution, a pair of mirrors disposed symmetrically to each other and adapted to deflect sideward the light reflected from the first mirror, and a plurality of condenser lens for focussing the light reflected from the paired mirrors onto each of the photoelectric converter elements, wherein irregularly reflected laser light of the directions other than the direction perpendicular to the longitudinal direction of the mark is extracted from all the scattered light resulting from the irradiation of the specimen surface with the laser beam and directed to the photoelectric converter elements, while the scattered light reflected in the direction perpendicular to the longitudinal direction of the mark is caused to pass through the paired mirrors at a region outside the reflecting regions thereof (an air-gap formed between the paired mirrors) so as not to reach the photoelectric converter element. By virtue of the arrangement described above, it becomes possible to detect with an enhanced reliability the presence of point defect of 3 $\mu$m in diameter (and/or 0.5 $\mu$m in depth) as well as linear defect of 2 $\mu$m in width on a surface of a specimen such as a blank material for a magnetic disc having a mark of fine recesses formed thereon.

DETAILED DESCRIPTION OF THE PREFERRED EMBODIMENTS

Now, the invention will be described in conjunction with exemplary embodiments thereof shown in the drawings in which like reference characters denote like or equivalent components, inclusive of those described hereinbefore.

Figure 9:
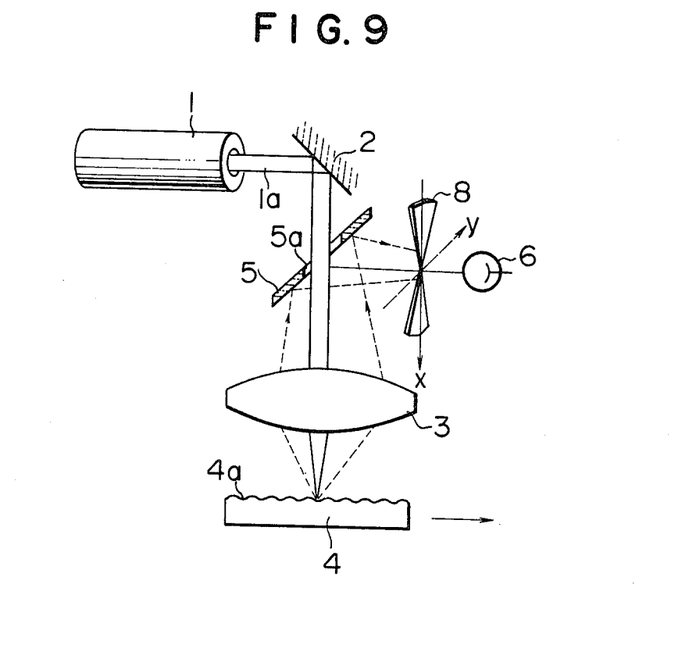
FIG. 9 is a view to show an exemplary embodiment of the inspecting apparatus for defecting the presence of defects, foreign substances or the like according to the invention.
Figure 20A:
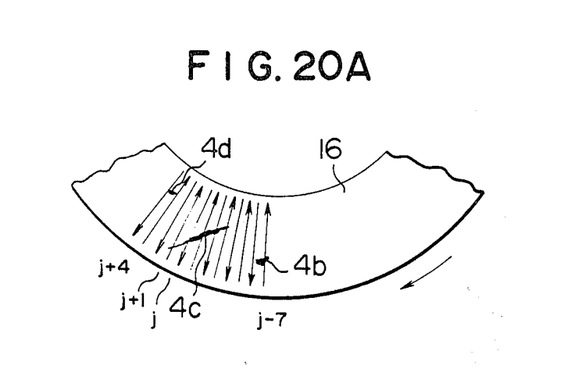
FIG. 20A illustrates the presence of point-like defects and a linear defect on a surface of a disc-like plate.

Referring at first to FIG. 9 which shows an inspecting apparatus according to a first embodiment of the invention, a pair of sector-like shielding plates 8 positioned symmetrically to each other in the x-direction with reference to the origin are disposed between a mirror 5 having a through-hole 5a for passing therethrough a laser beam 1a produced from a laser oscillator 1 and a photoelectric tube 6 which constitutes a photoelectric converter element, so that a major portion of scattered light reflected by a cutting mark 4a in the x-direction is intercepted by the shielding plates 8. Since the major portion of the irregularly scattered light reflected from the cutting mark 4a is intercepted by the shielding plates 8, while only the scattered light reflected from defects 4b; 4c (refer to FIG. 20A) present on a surface of a specimen 4 is allowed to impinge onto the photoelectric tube 6, a detection signal of a significantly improved S/N ratio can be obtained from the photoelectric tube 6 to thereby permit the detection of the imperfections or defects, foreign substances and the like to be accomplished with a high sensitivity and reliability.

Figure 10:
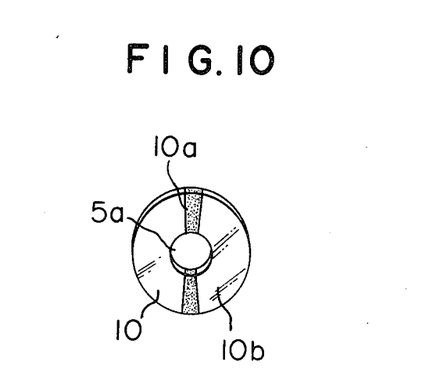
FIG. 10 shows a mirror assembly serving also for light shielding function for use in place of a mirror shown in FIG. 9.
Figure 11A:
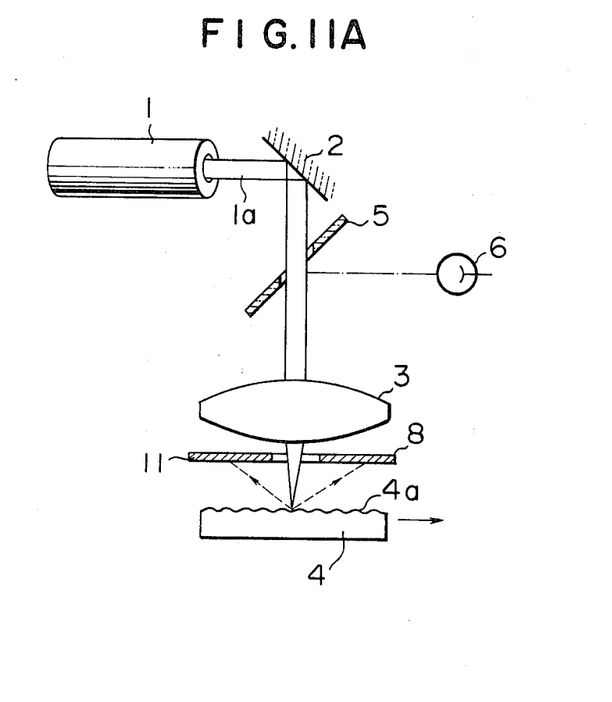
FIGS. 11A and 11B illustrate another embodiment of the inspecting apparatus for detecting defects, foreign substances or the like on a specimen surface according to the invention.
Figure 11B:
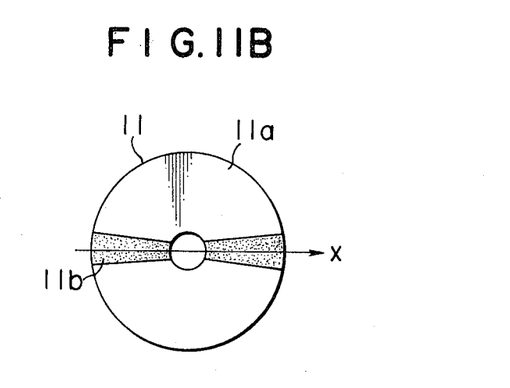

In place of the mirror 5 shown in FIG. 9, a mirror 10 can be used which has a pair of sector-like portions 10a positioned symmetrically to a center of the mirror in the x-direction and colored in black to reduce remarkably the reflection factor at these portions, while the other portions 10b are imparted with a high reflection factor, as shown in FIG. 10. In this case, the shielding plates 8 can be spared, since the mirror 10 serves also for the function of the shielding plates 8. Further, a shielding disc 11 which includes a pair of sector-like shielding portions 11a positioned symmetrically in the x-axis direction and other transparent portions 10b, as shown in FIG. 11B, may be disposed between the focussing lens 3 and the specimen 4, as is shown in FIG. 11A. In this case, the sector-like shielding plates 8 shown in FIG. 9 can be spared. Since the major portion of light scattered by the cutting mark is intercepted also in the arrangement shown in FIGS. 11A and 11B, the offset of the voltage signal output from the photoelectric tube shown in FIG. 6 can be reduced with the S/N ratio being significantly improved, to thereby assure detection of defects, foreign substances and the like present on the surface of the specimen 4 with a high sensitivity and reliability.

Figure 12A:
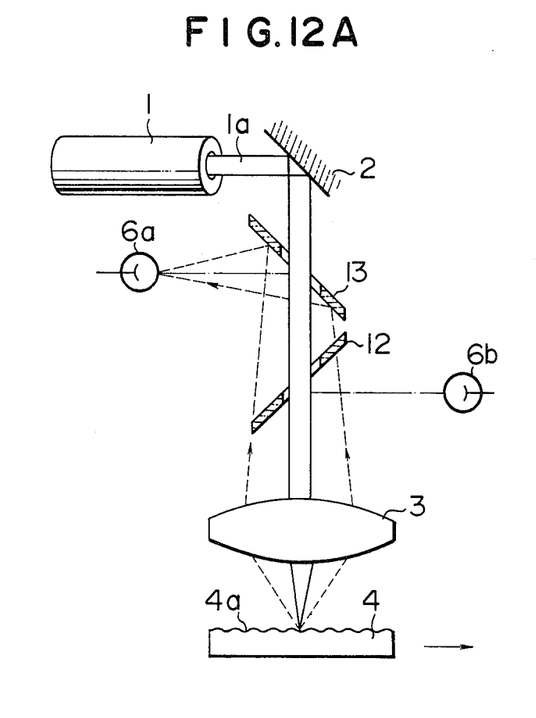
FIGS. 12A and 12B show still another embodiment of the inspecting apparatus according to the invention which is capable of detecting even those defects which extend in parallel to a cutting mark.
Figure 12B:
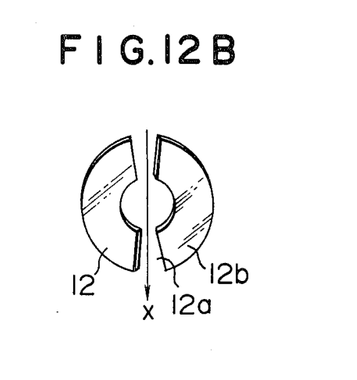
Figure 13:
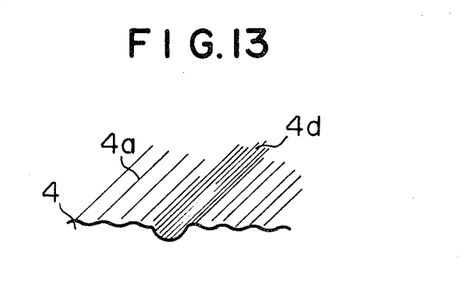
FIG. 13 illustrates a situation where a defect is present in parallel with the cutting mark.
Figure 14:
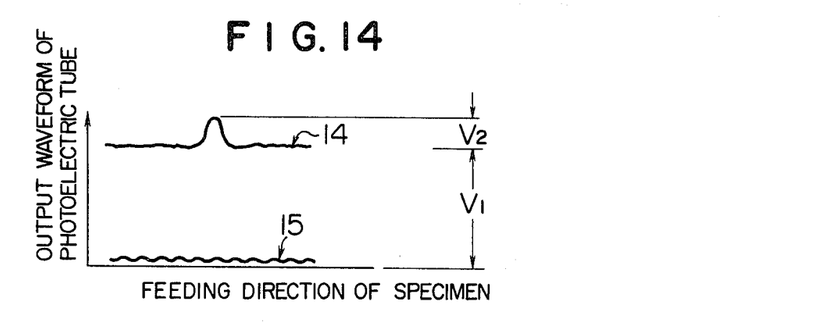
FIG. 14 graphically illustrates waveforms of video or image signals output from the photoelectric converter elements provided in the apparatus shown in FIG. 12 in response to the presence of a defect extending in parallel with the cutting mark.

It is often observed that a defect 4d shown in FIG. 13 is produced as extending in parallel with the grooves or recesses of the cutting mark due to a rolling action of a cutting tool. In order to make it possible to detect such defect 4d, a mirror 13 and a photoelectric tube 6a such as a photoelectric multiplier are provided, while a mirror 12 having a pair of sector-like transmitting portions 12a positioned symmetrically in the x-direction and the other reflecting portions 12b as shown in FIG. 12B is interposed between a mirror 13 and the focussing lens 3 so that the light scattered irregularly by the cutting mark 4a and the defect 4d extending in parallel thereto is deflected by the mirror 13 to reach the photoelectric tube 6a after having been transmitted through the transmitting portions 12a of the mirror 12, as is shown in FIG. 12A. Then, the signal voltage output from the photoelectric tube 6a which represents the presence of the parallel defect 4d exhibits such characteristic as illustrated by a curve 14 in FIG. 14 in which $V_1$ represents the output voltage corresponding to the cutting mark and $V_2$ represents the output voltage ascribable to the presence of the defects 4d extending in parallel with the cutting mark. Since the light scattered by the cutting mark and the defect 4d extending in parallel thereto is not reflected by the mirror 12 but is transmitted through the transmitting portion 12a, the output voltage of the photoelectric tube 6b exhibits such characteristic as represented by a curve 15 shown in FIG. 14. When the point-like discrete defect 4b and/or linear defect 4c (refer to FIG. 20A) is present on the surface of the specimen 4, it will be detected by the photoelectric tube 6b. In this manner, with the arrangement shown in FIG. 12A, the presence of the defect 4d extending in parallel to the cutting mark is detected by the photoelectric tube 6a, while the presence of the point-like defect 4b and/or the linear defect 4c is detected by the photoelectric tube 6b independently from the detection of the defect 4d. In the following, description will be made in concrete on the method and the apparatus for detecting the presence of defects, contaminants or the like on a surface of a disc-like aluminum plate for a magnetic disc by referring to FIGS. 15 to 21.

Figure 15:
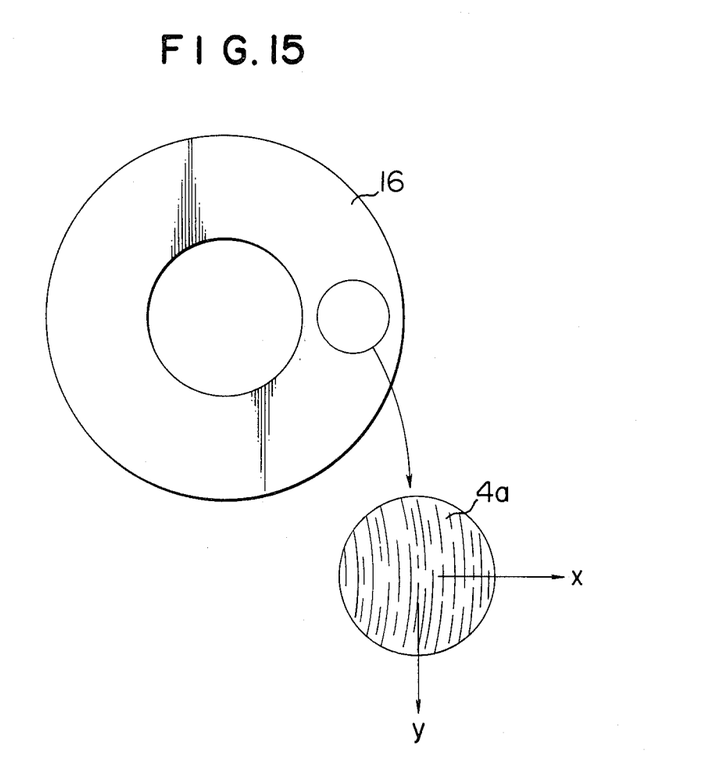
FIG. 15 shows a disc-like plate of aluminium for a magnetic disc employed as the specimen in carrying out the invention.
Figure 16:
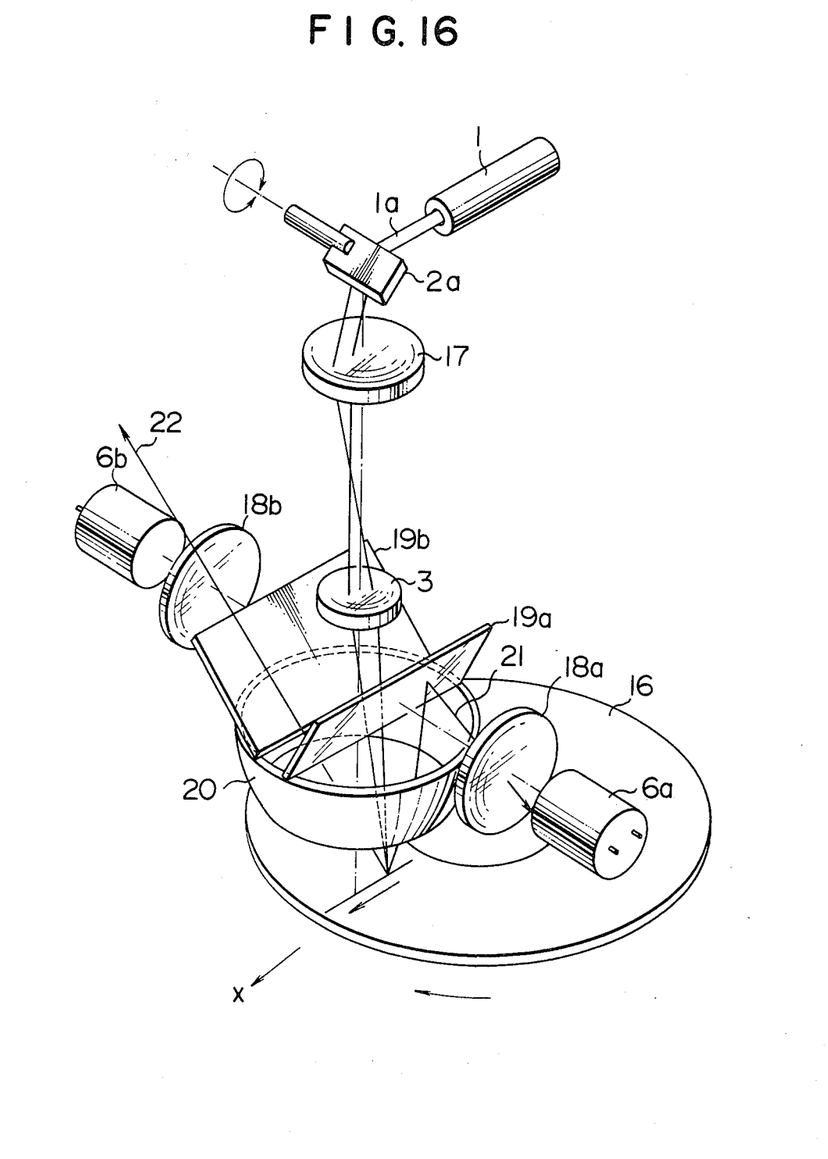
FIG. 16 shows a further embodiment of the inspecting apparatus according to the invention which is capable of detecting a point-like defect, linear defect or the like present on the surface of the aluminum disc shown in FIG. 15.
Figure 17:
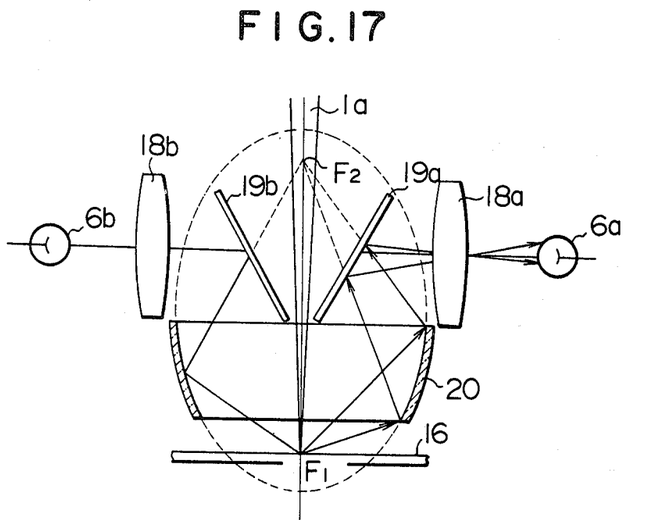
FIG. 17 illustrates the principle of collecting light by means of a mirror having an inner ellipsoidal mirror surface of revolution.

Since the aluminum disc 16 for a magnetic recording disc has circular cutting marks 4a as shown in FIG. 15 formed on a surface, a major portion of the irregularly reflected light scattered by the cutting marks will be produced in the radial direction of the disc. In the case of the inspecting apparatus being described, discrimination between the linear defect 4c and the point-like defect 4b (FIG. 20A) is effected by making use of a two-dimensional memory pattern described hereinafter. All the scattered light except for the light scattered in the direction perpendicular to the cutting mark 4a is focused to the photoelectric tubes 6a, 6b. FIG. 16 shows an exemplary embodiment of the apparatus destined for inspecting the aluminum disc plate 16. The laser beam 1a produced from a laser device 1 is reflected by an oscillating mirror or galvano mirror 2a driven by a galvanometer drive (not shown) as indicated by a double-headed arrow, whereby the disc plate 16 is scanned with the laser beam 1a in the radial direction. More particularly, the laser beam 1a reflected by the oscillating mirror 2a is focused through a field lens 17 and the focusing lens 3 to thereby form a spot on the surface of the disc plate 16 which is rotated at a constant speed. Light 21 scattered by a defect on the disc plate 16 is directed to the photoelectric tube 6a through a mirror 20 having an inner mirror surface in the form of an ellipsoid of revolution, a pair of mirrors 19a, 19b disposed symmetrically relative to the x-axis (i.e. the scanning direction of the laser beam) and condenser lens 18a. Light 22 scattered by the cutting mark 4a passes through an aperture defined between the paired mirrors 19a, 19b. FIG. 17 illustrates the light reflecting principle of a concave mirror 20 having the inner mirror surface in the form of an ellipsoid of revolution. This mirror will be referred to also as ellipsoidal mirror for simplification. In FIG. 17, symbols $F_1$ and $F_2$ represent focal points of the ellipsoidal mirror 20. The light collecting mirror assembly including the ellipsoidal mirror 20 and the paired mirrors 19a, 19b is so arranged and disposed that all the irregularly reflected light 21 scattered by the defect will impinge on the photoelectric tube 6a over the whole scanning range. It should be mentioned here that the ellipsoidal mirror (i.e. the mirror having an inner mirror surface in the form of an ellipsoid of revolution) may be replaced by a mirror having an inner reflecting surface in the form of a paraboloid of revolution (or paraboloidal mirror) to the substantially same effect. When the mirror of the last mentioned type is used, the reflected light becomes collimated. Accordingly, all the collimated light is reflected by the mirrors 19a, 19b to be focused on a light receiving area of the photoelectric tubes 6a, 6b through the condenser lenses 18a, 18b.

Figure 18:
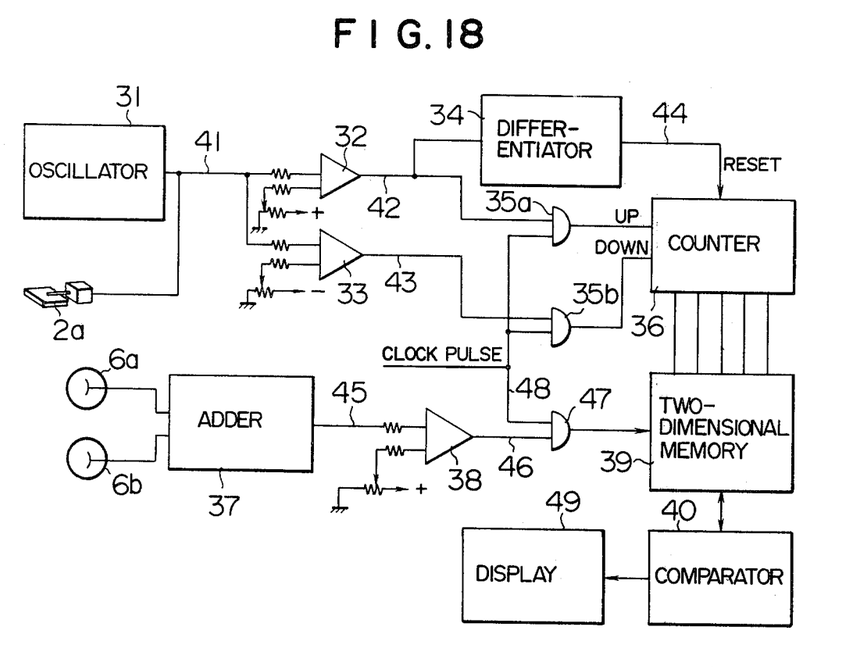
FIG. 18 shows an arrangement of a circuit to be used in combination with the inspecting apparatus shown in FIG. 16.
Figure 19:
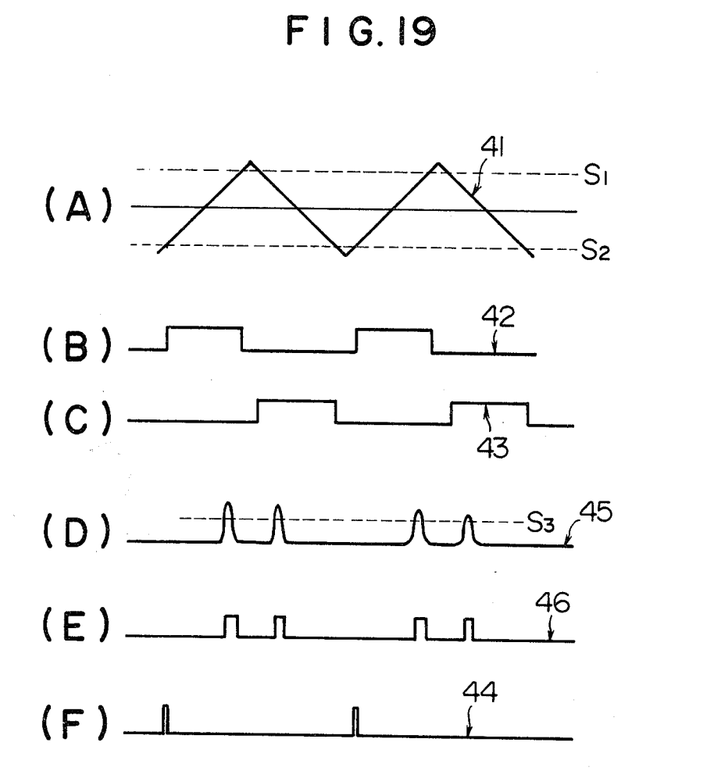
FIGS. 19(A), 19(B), 19(C), 19(D), 19(E) and 19(F) illustrate graphically waveforms of signals produced from the circuit shown in FIG. 16.
Figure 20B:
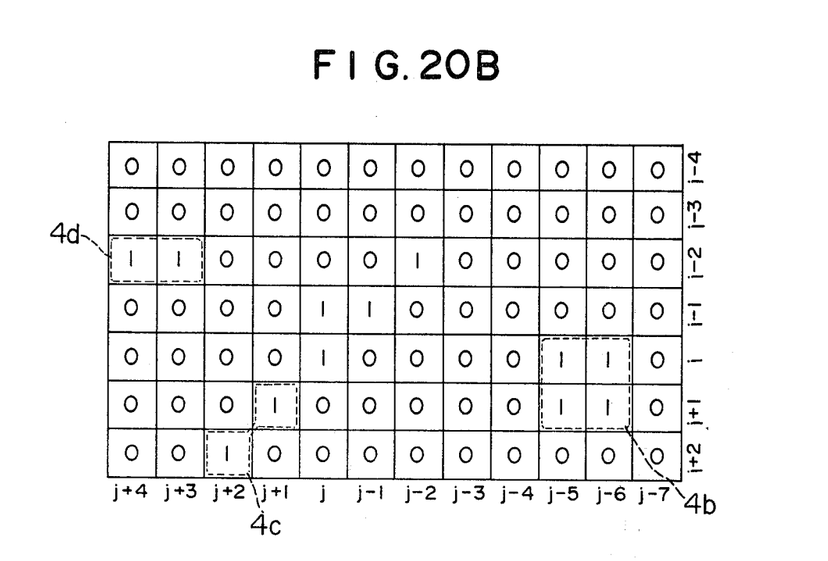
FIG. 20B illustrates a two-dimensional pattern stored in a memory used in the circuit arrangement shown in FIG. 18.
Figure 21A:
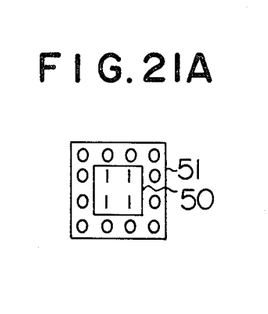
FIGS. 21A and 21B illustrate a manner in which the point-like defect and the linear defect are discriminated by a computer.
Figure 21B:
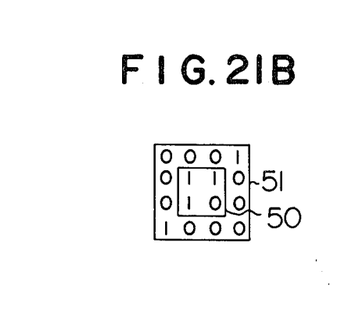

Next, a circuit arrangement for processing and evaluating the defect detection signal by using a two-dimensional memory in which a pattern of a defect is stored will be described by referring to FIGS. 18 and 19. A scanning signal 41 of a saw-tooth waveform (refer to FIG. 19(A)) produced from an oscillator circuit 31 for oscillating the mirror 2a to effect the scanning of the disc plate 16 by the laser beam 1a is encoded into binary signals with reference to predetermined threshold values $S_1$ and $S_2$ in a binary encoder circuits 32 and 33, respectively. The binary signals thus produced constitute a right scanning validation interval signal 42 (FIG. 19(B)) and a left scanning validation interval signal (FIG. 19(C)), respectively. The signals output from the photoelectric tubes 6a, 6b are added together through an adder circuit 37 to thereby constitute a video or image signal 45 shown in FIG. 19(D). The video or image signal 45 is encoded into a binary signal with reference to a predetermined threshold $S_3$ in a binary encoder circuit 38. The binary signal thus produced is applied to one input of an AND gate 47 having the other input supplied with a clock pulse signal 48. The output signals of the AND circuit 47 each representative of a sampled pattern element is stored in a two-dimensional memory 39. On the other hand, the rising edge of the right scanning validation interval signal 42 is differentiated by a differentiator circuit 34 into a pulse which is applied to an up-down counter 36 as the reset signal shown in FIG. 19(F). This counter 36 serves to designate addresses of the memory 39 at which the binary pattern element signals are stored. The count contents of this counter 36 is incremented by the signal produced from a gate circuit 35a during the right scanning validation interval, and decremented by the signal produced from a gate circuit 35b during the left scanning validation interval or period. The counter 36 is reset by the reset signal RESET produced by the differentiator circuit 34 described above. Accordingly, the sequence of addresses of the memory 39 designated by the counter 36 during the right scanning validation interval is in reverse to the sequence of the addresses designated by the counter 36 during the left scanning validation interval, so that the addresses allotted to particular pattern elements stored in the two-dimensional pattern in the memory 39 remain same independently from the scanning directions. FIG. 20B shows examples of the two-dimensional patterns of a point-like defect and a linear defect. As can be seen from this figure, the defect of a linear form is represented by a relatively long succession of logic "1", while the defect of a point-like form is represented by a smaller number of logic "1" in succession. By determining the length of a continuous train of logic "1" with the aid of a computer 40, it is possible to discriminate the point defect 4b and the linear defect 4c from each other. In this manner, inspection of the aluminum disc plate 16 having a mark composed of fine recesses arrayed in a predetermined direction can be made to detect the presence of the point-like defect 4b and/or the linear defect 4c while discriminating these defects from each other. For example, definition may be made such that an array of logic "1's" at 2×2 adjacent addresses represents the point-like defect, while an array of logic "1's" at a greater number of successive addresses than 2×2 represents the linear defect. Under the conditions, the discrimination of the types of defects can be effected in the computer 40 by making use of an inner frame 50 and an outer frame 51 shown in FIGS. 21A and 21B. The point-like defect is then identified by the concentrated distribution of logic "1's" within the inner frame, as shown in FIG. 21A, while the linear defect can be identified by a succession of the logic "1" over the inner frame 50 and the outer frame 51. The discrimination of the defect is summarized in the following table.

TABLE

|  | No Defect | Point Defect | Linear Defect |
|---|---|---|---|
| Logical sum within a frame of 2 × 2 | 0 | 1 | 0 or 1 |
| Logical sum outside a frame of 2 × 2 | 0 | 0 | 1 |

For discrimination, the computer 40 shifts a sub-matrix of 4×4 addresses (in row and column) successively over the whole area of the pattern stored in the memory 39 to discriminatively determine the point-like defect and the linear defect on the basis of the logical sum within and outside the 2×2 array described above. The results of determination are supplied to a display circuit 49 to be displayed.

As will be appreciated from the foregoing description, the present invention now makes it possible to detect with an increased sensitivity and reliability the presence of the point-like defects and/or the linear defects present on a surface of a specimen on which fine marks such as cutting marks are formed in a predetermined direction. In a practical example, a point-like defect of 3 $\mu$m in diameter (0.5 $\mu$m in width) as well as a linear defect of 2 $\mu$m in line width on a specimen surface can be detected by scanning the specimen surface with a laser beam focused to a light spot of 50 $\mu$m in diameter.

In this connection, it will be understood that, as the spot diameter of the laser beam is decreased, the presence of the defect and/or foreign substance of finer sizes can be detected. However, since the scanning over the whole surface of the specimen takes a correspondingly increased time, the inspection rate is lowered. Such being the circumstances, the diameter of the laser spot should preferably be selected at 50 $\mu$m which defines approximately the upper limit of a range in which the point-like defect of 3 $\mu$m in diameter and the linear defect of 2 $\mu$m in width can be detected.

We claim:
1. An apparatus for inspecting a defect or the like on a surface of a disc having a cutting mark constituted by fine grooves extending in the circular direction of the disc and with random intervals in the radial direction of the disc, the apparatus comprising:
   laser oscillator means for producing a laser beam;
   laser spot irradiation means for irradiating the surface of the disc with the laser beam in the form of a focused laser spot projected substantially perpendicularly to the plane of the disc surface, whereby defects or the like on the surface of the disc cause light of the focused laser spot to be irregularly scattered therefrom;
   scanning means including laser scanning means for scanning the laser spot in the radial direction of the disc and rotation driving means for rotating the disc and for two-dimensionally scanning the surface of the disc with the laser spot;
   photoelectric converter means including a plurality of photoelectric converters;
   optical means for conducting light irregularly scattered by defects or the like other than the cutting mark on the disc along light detecting path means of said plurality of photoelectric converters, said optical means including a first mirror having a concave inner mirror surface of revolution and disposed with respect to the surface of the disc so as to reflect light irregularly scattered therefrom, a pair of second mirrors associated with said first mirror and disposed symmetrically to each other for deflecting irregularly scattered light reflected by said first mirror which is in a direction other than the radial direction of the disc into the light detecting path means of said plurality of photoelectric converters and for permitting light reflected from the cutting mark to pass out of the light detecting path means of said plurality of photoelec- tric converters, and a plurality of condenser lenses for focusing light reflected by said pair of second mirrors onto said plurality of photoelectric converters, said plurality of photoelectric converters providing output signals in response to the light detected thereby, and adding circuit means for adding the output signals of said plurality of photoelectric converters to produce an output signal indicative of the presence or absence of a defect or the like on the surface of the disc.

2. An apparatus according to claim 1, wherein said first mirror has the concave inner mirror surface in the form of an ellipsoidal surface of revolution.

3. An apparatus according to claim 1, wherein said first mirror has the concave inner mirror surface in the form of a paraboloidal surface of revolution.

4. An apparatus according to claim 1, wherein said first mirror has an aperture therethrough and disposed with the axial center thereof located on an optical axis of the apparatus, and said pair of second mirrors are symmetrically disposed with respect to the scanning direction of the focused laser spot for sidewardly deflecting the light reflected by said first mirror into the light detecting path means of said plurality of photoelectric converters.

5. An apparatus according to claim 4, wherein said pair of second mirrors are spaced from one another and disposed with respect to the aperture of said first mirror for permitting light reflected from said cutting mark to pass between said pair of second mirrors and out of the light detecting path means of said plurality of photoelectric converters.

6. An apparatus according to claim 1, 2 or 3, further including a binary encoding and quantizing circuit for binary encoding a picture signal derived from said photoelectric converter means with reference to at least one predetermined threshold level and quantizing into picture elements by a sampling signal, a two-dimensional memory for storing the binary picture element signals outputted from said binary encoder and quantizing circuit at respective addresses in a two-dimensionally array, means for determining a first logic sum of binary signals stored at addresses in an n×m array of n rows and m columns, determining a second logic sum of binary signals stored at addresses located externally around said n×m array, and discriminating defects or the like in respect of forms thereof in dependence on said first and second logic sums.

* * * * *